US008404876B2

(12) United States Patent
Sharma et al.

(10) Patent No.: US 8,404,876 B2
(45) Date of Patent: Mar. 26, 2013

(54) PROCESS FOR PRODUCING NANOPARTICLES

(75) Inventors: Neeraj Sharma, Woodbury, MN (US); Choua C. Vu, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 351 days.

(21) Appl. No.: 12/989,452

(22) PCT Filed: May 6, 2009

(86) PCT No.: PCT/US2009/043006

§ 371 (c)(1), (2), (4) Date: Oct. 25, 2010

(87) PCT Pub. No.: WO2009/137595

PCT Pub. Date: Nov. 12, 2009

(65) Prior Publication Data

US 2011/0046404 A1 Feb. 24, 2011

Related U.S. Application Data

(60) Provisional application No. 61/051,477, filed on May 8, 2008, provisional application No. 61/051,468, filed on May 8, 2008.

(51) Int. Cl.
C07F 7/18 (2006.01)
C07F 9/02 (2006.01)
C01B 25/26 (2006.01)

(52) U.S. Cl. .............. 556/9; 556/10; 556/405; 977/840; 423/308

(58) Field of Classification Search ................ 556/9, 10, 556/405; 423/308; 977/840
See application file for complete search history.

(56) References Cited

U.S. PATENT DOCUMENTS

| | | | |
|---|---|---|---|
| 6,355,271 | B1 | 3/2002 | Bell et al. |
| 6,426,114 | B1 | 7/2002 | Troczynski et al. |
| 2003/0032192 | A1 | 2/2003 | Haubold et al. |
| 2004/0170699 | A1 | 9/2004 | Chane-ching et al. |
| 2004/0241101 | A1 | 12/2004 | Baran et al. |
| 2004/0242729 | A1 | 12/2004 | Baran et al. |
| 2006/0199886 | A1 | 9/2006 | Ryang |
| 2006/0257306 | A1 | 11/2006 | Yamamoto et al. |
| 2007/0196259 | A1 | 8/2007 | Stark et al. |
| 2007/0196509 | A1 | 8/2007 | Riman et al. |
| 2011/0039947 | A1 | 2/2011 | Sharma et al. |

FOREIGN PATENT DOCUMENTS

| | | |
|---|---|---|
| WO | WO 03/095085 | 11/2003 |
| WO | WO 2008/033718 | 3/2008 |

OTHER PUBLICATIONS

Lemos et al., "A method for simultaneously precipitating and dispersing nano-sized calcium phosphate suspensions," Key Engineering Materials, vol. 284-286, pp. 67-70 (2005).
Yubao et al., "Preparation and characterization of nanograde osteoapatite-like rod crystals," Journal of Materials Science: Materials in Medicine, vol. 5, pp. 252-255 (1994).
Layrolle et al., "Characterization and reactivity of nanosized calcium phosphates prepared in anhydrous ethanol," Chemistry of Materials, vol. 6, pp. 1996-2004 (1994).
Layrolle et al., "Sol-gel synthesis of amorphous calcium phosphate and sintering into microporous hydroxyapatite bioceramics," Journal of the American Ceramic Society, vol. 81(6), pp. 1421-1428 (1998).
Mai et al, "Orderly Aligned and Highly Luminescent Monodisperse Rare-Earth Orthophosphate Nanocrystals Synthesized by a Limited Anion-Exchange Reaction," Chemistry of Materials 19, 4514-4522 (2007).
Riman et al. "Solution synthesis of hydroxyapatite designer particulates," Solid State Ionics, vol. 151, pp. 393-402 (2002).
Vallet-Regi et al., "Hydroxyapatite Particles Synthesized by Pyrolysis of an Aerosol," J. Solid State Chemistry, vol. 112, pp. 58-64 (1994).
López-Macipe et al., "Nanosized Hydroxyapatite Precipitation from Homogeneous Calcium/ Citrate/Phosphate Solutions Using Microwave and Conventional Heating," Advanced Materials, vol. 10, pp. 49-53 (1998).
Sadasivan et al., "Synthesis of calcium phosphate nanofilaments in reverse micelles," Chemistry of Materials, vol. 17, pp. 2765-2770 (2005).
Stouwdam et al., "Improvement in The Luminescence Properties and Processability of LaF3/Ln and LaPO4/Ln Nanoparticles by Surface Modification," Langmuir 20, 11763 (2004).
Yao et al., "Hydroxyapatite nanostructure material derived using cationic surfactant as a template," Journal of Materials Chemistry, vol. 13, pp. 3053-3057 (2003).
Welzel et al., "Continuous preparation of functionality calcium phosphate nanoparticles with adjustable crystallinity," Chemical Communications, pp. 1204-1205 (2004).
Qi et al., "Microemulsion-Mediated Synthesis of Calcium Hydroxyapatite Fine Powders," Journal of Materials Science Letters, vol. 16, No. 21, pp. 1779-1781 (1997).
Fowler et al., "Influence of Surfactant Assembly on the Formation of Calcium Phosphate Materials—A Model for Dental Enamel Formation," Journal of Materials Chemistry, vol. 15, pp. 3317-3325 (2005).
Liou et al., "Manipulation of Nanoneedle and Nanosphere Apatite/ Poly(Acrylic) Nanocomposites," Journal of Biomedical Materials Research-Part B Applied Biomaterials, vol. 73(1), pp. 117-122 (2005).
D'Andrea et al., "Covalent Surface Modification of Calcium Hydroxyapatite Using N-Alkyl and N-Fluoroalkylphosphonic Acids," Langmuir, vol. 19, pp. 7904-7910 (2003).
Tanaka et al., "Surface Modification of Calcium Hydroxyapatite With Hexyl and Decyl Phosphates," Colloids and Surfaces A: Physicochemical and Engineering Aspects, vol. 125, pp. 53-62 (1997).

(Continued)

*Primary Examiner* — Porfirio Nazario Gonzalez
(74) *Attorney, Agent, or Firm* — Lucy C. Weiss

(57) ABSTRACT

A process comprises (a) combining (1) at least one metal cation source, (2) at least one phosphate anion source, (3) at least one organic base comprising at least one organic moiety comprising at least about five carbon atoms, and (4) at least one organosilane comprising at least one organic moiety comprising at least about six carbon atoms; and (b) allowing the metal cation source and the phosphate anion source to react in the presence of the organic base and the organosilane (for example, to form surface-modified metal phosphate nanoparticles).

20 Claims, No Drawings

OTHER PUBLICATIONS

Tanaka et al., "Surface Structure and Properties of Calcium Hydroxyapatite Modified by Hexamethyldisilazane," Journal of Colloid and Interface Science, vol. 206, pp. 205-211 (1998).

Cai et al., "Role of Hydroxyapatite Nanoparticle Size in Bone Cell Proliferation," Journal of Materials Chemistry, vol. 17. pp. 3780-3787 (2007).

Loher et al., "Fluoro-Apatite and Calcium Phosphate Nanoparticles by Flame Synthesis," Chemistry of Materials, vol. 17(1), pp. 36-42 (2005).

Roether et al., "The Effect of Surface Treatment of Hydroxyapatite on The Properties of a Bioactive Bone Cement," Journal of Materials Science: Materials in Medicine, Kluwer Academic Publishers, BO, vol. 15, No. 4, (Apr. 1, 2004), pp. 413-418.

Dupraz et al., "Characterization of Silane-Treated Hydroxyapatite Powders for Use as Filler in Biodegradable Composites," Journal of Biomedical Materials Research, vol. 30, (1996).

Balasundaram et al., "Using Hydroxyapatite Nanoparticles and Decreased Crystallinity to Promote Osteoblast Adhesion Similar to Functionalizing With RGD," Biomaterials, Elsevier Science Publishers BV., Barking, GB, vol. 27, No. 14, (May 1, 2006), pp. 2798-2805.

Balasundaram et al., "Applications of Magnetic Nanoparticles for the Treatment of Ostheoporosis" Materials Research Society Symposium Proceedings, vol. 1019, (2007), p. FF02, XP002564515.

International Search Report, International Application No. PCT/US2009/043006, International Filing Date: May 6, 2009.

PROCESS FOR PRODUCING NANOPARTICLES

STATEMENT OF PRIORITY

This application claims the priorities of U.S. Provisional Applications Nos. 61/051,477 and 61/051,468, both filed May 8, 2008, the contents of which are hereby incorporated by reference.

FIELD

This invention relates to processes for producing metal phosphate particles.

BACKGROUND

Metal phosphates (for example, alkaline earth phosphates such as magnesium phosphate and calcium phosphate) have numerous applications. Alkaline earth phosphates are used in anti-rust coatings, in flame retardants, in antacids, and in producing fluorescent particles. Iron phosphates find application in cathode material for lithium ion batteries. Aluminum, manganese, cobalt, tin, and nickel phosphates are used in heterogeneous catalysis. Zinc phosphate is commonly used as a pigment in anti-corrosion protection. Zirconium phosphates are used as solid acid catalysts. Various lanthanide phosphates are useful as fluorescent and laser materials.

Calcium phosphates are particularly useful, however, due to their classification as biocompatible materials. Under physiological conditions calcium phosphates can dissolve, and the resulting dissolution products can be readily assimilated by the human body. Biocompatible calcium phosphates include hydroxyapatite (HAP; $[Ca_5(PO_4)_3OH]$), dicalcium phosphate (DCP; $[Ca(HPO_4).2H_2O]$), tricalcium phosphate (TCP; $[Ca_3(PO_4)_2]$), tetracalcium phosphate (TTCP, $[Ca_4O(PO_4)_2]$), and amorphous calcium phosphate.

Of the biocompatible calcium phosphates, hydroxyapatite can be more stable under physiological conditions. Thus, hydroxyapatite has been used for bone repair after major trauma or surgery (for example, in coatings for titanium and titanium alloys). Hydroxyapatite has also been used in the separation and purification of proteins and in drug delivery systems. Other calcium phosphates have been used as dietary supplements in breakfast cereals, as tableting agents in some pharmaceutical preparations, in feed for poultry, as anti-caking agents in powdered spices, as raw materials for the production of phosphoric acid and fertilizers, in porcelain and dental powders, as antacids, and as calcium supplements.

For some of these applications (for example, adjuvants for vaccines, cores or carriers for biologically active molecules, controlled release matrices, coating implant materials, protein purification, and dental applications), non-agglomerated nanoparticles of calcium phosphate can be desired. The preferred sizes, morphologies, and/or degrees of crystallinity of the nanoparticles vary according to the nature of each specific application.

Numerous methods have been used for the synthesis of hydroxyapatite nanoparticles including chemical precipitation, hydrothermal reactions, freeze drying, sol-gel formation, phase transformation, mechanochemical synthesis, spray drying, microwave sintering, plasma synthesis, and the like. Hydroxyapatite nanoparticles have often been synthesized by the reaction of aqueous solutions of calcium ion-containing and phosphate ion-containing salts (the so-called "wet process"), followed by thermal treatment. Nanoparticles obtained by this method generally have had a needle-like (acicular) morphology with varying degrees of crystallinity, depending upon the nature of the thermal treatment. Such acicular nanoparticles can be used as coating implant materials but have limited or no use in some of the other applications mentioned above.

Various additives have been used to control hydroxyapatite particle growth and/or to alter hydroxyapatite particle morphology but with only limited success. For example, polymers and solvent combinations have been used in the above-described wet process to suppress crystal growth along one axis, but only a few approaches have provided particles with decreased aspect ratios or particles of spherical morphology but relatively large particle size.

Solid-state reaction of precursors, plasma spraying, pulsed laser deposition, and flame spray pyrolysis methods have resulted in hydroxyapatite nanoparticles of different morphologies (for example, spherical or oblong), but these have often been in the form of micron-sized agglomerates of nanoparticles that have been of limited use in certain applications. Numerous researchers have carried out post-synthesis surface modification of hydroxyapatite to de-agglomerate the particles.

Surfactant-based systems have also been widely used in the synthesis of hydroxyapatite nanoparticles. For example, hydroxyapatite nanoparticles have been prepared by an emulsion process in which reverse micelles are produced in an oil phase by using a surface-active agent, followed by the reaction of phosphate and calcium ions in a water phase in the micelles. Disadvantages of such "water in oil" reverse microemulsion processes include the use of relatively large amounts of oil and surfactant (resulting in the need for recycling these materials or, alternatively, accepting a relatively low production yield) and the need for appropriate disposal of nonbiodegradable surfactants.

Generally the synthesis of spherical hydroxyapatite nanoparticles has involved the use of either surfactants or polymers to control the morphology and the size of the resulting particles. The capability of such methods to provide nanoparticles in the form of redispersible dry powder (for example, dry powder that can be redispersed in an appropriate solvent to provide a non-agglomerated nanoparticle dispersion), however, has generally not been evident.

Thus, current processes for the preparation of nanosized calcium phosphate particles can utilize expensive starting materials (for example, calcium alkoxide), can require the use of surfactants, can be complex, can provide agglomerates, can provide slow particle growth, can provide insufficient control over particle size and/or particle morphology, can fail to provide often preferred particle sizes (for example, average primary particle diameters of about 1 to about 50 nm), and/or can fail to provide nanoparticles that are redispersible.

SUMMARY

Thus, we recognize that there is a need for processes for producing metal phosphate nanoparticles (particularly, calcium phosphate nanoparticles) that can minimize or even eliminate particle agglomeration, while allowing for particle growth to desired primary particle sizes. Preferred processes will be simple, will be cost-effective, will enable control of final particle size and/or morphology, and/or will provide nanoparticles that are redispersible. In particular, we recognize that there is a need for very small nanoparticles (for example, having average primary particle diameters of less than about 20 nm) that are biocompatible and preferably of spherical morphology, which can be effectively used in, for example, inhalable aerosol drug delivery systems.

Briefly, in one aspect, this invention provides a process, which comprises (a) combining (preferably, in at least one solvent) (1) at least one metal cation source, (2) at least one phosphate anion source, (3) at least one organic base comprising at least one organic moiety comprising at least about five carbon atoms, and (4) at least one organosilane comprising at least one organic moiety comprising at least about six carbon atoms; and (b) allowing the metal cation source and the phosphate anion source to react in the presence of the organic base and the organosilane (for example, to form surface-modified metal phosphate nanoparticles). Preferably, the metal cation source is a metal salt comprising at least one metal cation and at least one anion that is capable of being displaced by phosphate anion, and/or the phosphate anion source is selected from phosphorus-containing compounds (for example, phosphoric acid or an organoammonium phosphate salt) that are capable of providing phosphate anion either directly or upon dissolution or dispersion (for example, in aqueous or non-aqueous solvent), oxidation, or hydrolysis, and combinations thereof.

It has been discovered that use of the above-described metal phosphate precursors including an organic base and an organosilane can enable the preparation of substantially non-agglomerated metal phosphate nanoparticles. The nanoparticles can be grown to preferred average primary particle sizes (for example, average primary particle diameters of about 1 nm to about 50 nm).

Surprisingly, the use of precursors including relatively long-chain organosilane surface modifier(s) can provide nanoparticles that are redispersible and preferably of substantially spherical morphology. Preferred embodiments of the process can enable control of average primary particle size and/or particle morphology by varying, for example, the reaction temperature, time, pH, choice and/or amounts of reactants, and/or the order and/or manner of combination of reactants.

Thus, the process of the invention can be especially advantageous for producing calcium phosphate nanoparticles. The process can be used to provide, for example, calcium phosphate nanoparticles having average primary particle diameters in the range of about 1 nm to about 20 nm. Such nanoparticles can be well-suited for use in various pharmaceutical, medical, and dental applications, particularly those (for example, inhalable aerosol drug delivery systems) requiring or desiring relatively small, redispersible, biocompatible nanoparticles of spherical morphology.

The process of the invention, in addition, is relatively simple and utilizes metal phosphate precursors (for example, metal cation source and phosphate anion source) that are relatively inexpensive starting compounds. Thus, in at least preferred embodiments, the process can meet the above-mentioned need in the art for simple, cost-effective processes for producing metal phosphate nanoparticles (particularly, calcium phosphate nanoparticles) that can minimize particle agglomeration, while allowing for particle growth to desired primary particle sizes, and that can provide nanoparticles that are redispersible.

DETAILED DESCRIPTION

In the following detailed description, various sets of numerical ranges (for example, of the number of carbon atoms in a particular moiety, of the amount of a particular component, and the like) are described, and, within each set, any lower limit of a range can be paired with any upper limit of a range.

DEFINITIONS

As used in this patent application:

"agglomeration" means an association of primary particles, which can range from relatively weak (based upon, for example, charge or polarity) to relatively strong (based upon, for example, chemical bonding);

"nanoparticles" means particles having a diameter of less than 100 nm;

"primary particle size or diameter" means the size or diameter of a non-associated single nanoparticle;

"redispersible" (in regard to nanoparticles) means nanoparticles that can be "dried" or precipitated from an original dispersion of the nanoparticles in aqueous or organic solvent or a combination thereof (for example, by removal of the solvent and/or by a change in solvent polarity) to form a powder or a wet precipitate or gel that can be dispersed again in the original dispersion solvent (or a solvent of essentially the same polarity as that of the original dispersion solvent) to provide a nanoparticle dispersion (preferably, without substantial change in primary particle size (and/or average particle size as measured by dynamic light scattering) relative to the original dispersion and/or without substantial sedimentation of the nanoparticles over a period of at least four hours (for example, with size change and/or sedimentation of less than 25 percent (preferably, less than 20 percent; more preferably, less than 15 percent; most preferably, less than 10 percent), where the sedimentation percentage is by weight, based upon the total weight of nanoparticles in the dispersion));

"sol" means a dispersion or suspension of colloidal particles in a liquid phase; and "substantially spherical" (in regard to nanoparticles) means at least a major portion of the nanoparticles have an aspect ratio less than or equal to 2.0 (preferably, less than or equal to 1.5; more preferably, less than or equal to 1.25; most preferably, 1.0).

Metal Cation Source

Metal cation sources suitable for use in the process of the invention include metal salts comprising at least one metal cation and at least one anion that can be displaced by phosphate anion. Such salts can be prepared in situ, if desired (for example, by the reaction of a metal hydroxide, a metal carbonate, or a metal oxide with a mineral acid). Useful metal cations include those of transition metals (including the lanthanides and the actinides thorium and uranium), alkaline earth metals, alkali metals, post-transition metals, and the like, and combinations thereof.

Preferred transition metals include titanium, vanadium, chromium, manganese, iron, cobalt, nickel, copper, zinc, yttrium, zirconium, niobium, molybdenum, ruthenium, cadmium, hafnium, tantalum, tungsten, lanthanum, cerium, neodymium, samarium, europium, gadolinium, terbium, dysprosium, erbium, ytterbium, thorium, and combinations thereof (more preferably, titanium, manganese, iron, cobalt, zinc, yttrium, zirconium, niobium, tantalum, lanthanum, cerium, europium, gadolinium, terbium, dysprosium, erbium, and combinations thereof; most preferably, manganese, iron, zinc, yttrium, zirconium, niobium, tantalum, lanthanum, cerium, europium, gadolinium, terbium, and combinations thereof). Preferred post-transition metals include aluminum, gallium, indium, tin, lead, antimony, bismuth, and combinations thereof (more preferably, aluminum, gallium, tin, antimony, bismuth, and combinations thereof; most preferably, aluminum).

Preferred alkaline earth metals include beryllium, calcium, strontium, magnesium, barium, and combinations thereof (more preferably, calcium, strontium, magnesium, barium, and combinations thereof even more preferably, calcium, magnesium, strontium, and combinations thereof; most preferably, calcium). Preferred alkali metals include lithium, sodium, potassium, rubidium, cesium, and combinations thereof (more preferably, lithium, sodium, potassium, and combinations thereof; most preferably, sodium, potassium, and combinations thereof).

Preferably, the metal cation is a divalent metal cation (more preferably, a divalent alkaline earth metal cation; even more preferably, divalent calcium or magnesium; most preferably, divalent calcium). Alkaline earth metals and combinations thereof are preferred.

Useful anions include halide, nitrate, acetate, carbonate, alkanoate (for example, formate, propionate, hexanoate, neodecanoate, and the like), alkoxide, lactate, oleate, acetylacetonate, sulfate, thiosulfate, sulfonate, bromate, perchlorate, tribromoacetate, trichloroacetate, trifluoroacetate, sulfide, hydroxide, oxide, and the like, and combinations thereof. Preferred anions include halide, nitrate, sulfate, carbonate, acetate, hydroxide, oxide, and combinations thereof (more preferably, halide, nitrate, acetate, and combinations thereof; most preferably, halide and combinations thereof).

Mixed metal salts, mixed anion salts, and/or mixtures of salts can be utilized, if desired. The salts can comprise other metal cations (for example, at levels up to about 10 mole percent, based upon the total number of moles of metal cation), but preferably all metals in the salts are selected from those described above. Similarly, the salts can comprise other anions (for example, at levels up to about 10 mole percent, based upon the total number of moles of anion), but preferably all anions in the salts are selected from those described above.

Representative examples of useful metal salts include calcium chloride hexahydrate, calcium chloride dihydrate, calcium chloride (anhydrous), calcium bromide hexahydrate, calcium nitrate tetrahydrate, calcium acetate monohydrate, calcium propionate, calcium lactate pentahydrate, calcium 2-ethylhexanoate, calcium methoxyethoxide, calcium carbonate, magnesium chloride hexahydrate, magnesium bromide hexahydrate, magnesium ethoxide, magnesium hydroxide, magnesium nitrate hexahydrate, magnesium acetate tetrahydrate, magnesium oleate, magnesium sulfate heptahydrate, zinc chloride (anhydrous), zinc acetate dihydrate, zinc carbonate hydroxide, zinc bromide dihydrate, zinc nitrate hexahydrate, zinc neodecanoate, zinc oxide, zinc sulfate heptahydrate, cobalt chloride hexahydrate, manganese (II) chloride tetrahydrate, manganese (II) bromide tetrahydrate, manganese (II) nitrate tetrahydrate, manganese (II) acetate tetrahydrate, manganese (III) acetylacetonate, europium (III) chloride hexahydrate, europium (III) nitrate hexahydrate, europium (II) chloride, europium (III) oxide, terbium (III) chloride hexahydrate, terbium (III) nitrate hexahydrate, terbium (III,IV) oxide, and the like, and combinations thereof. More preferred metal salts include those having anions selected from halide, nitrate, acetate, and combinations thereof. The halides are most preferred. Hydrated metal salts can be preferred (for example, to facilitate hydrolysis of the organosilane).

Such metal salts can be prepared by known methods. Many of such salts are commercially available.

Phosphate Anion Source

Phosphate anion sources suitable for use in the process of the invention include phosphorus-containing compounds that provide phosphate anion either directly or upon dissolution or dispersion (for example, in aqueous or non-aqueous solvent), oxidation, or hydrolysis, and combinations thereof. Such compounds include phosphoric acid ($H_3PO_4$); phosphorous acid ($H_3PO_3$); hypophosphorous acid ($H_3PO_2$); thiophosphoric acid; phosphoric acid esters; thiophosphoric acid esters (for example, diethylchlorothiophosphate, diethyldithiophosphate, ethyldichlorothiophosphate, trimethylthiophosphate, and the like); phosphite esters (for example, dimethylphosphite, trimethylphosphite, diisopropylphosphite, diethylhydrogenphosphite, diisobutylphosphite, dioleylhydrogenphosphite, diphenylhydrogenphosphite, triphenylphosphite, ethylenechlorophosphite, tris(trimethylsilyl) phosphite, and the like); thiophosphite esters (for example, trilauryltrithiophosphite, triethyltrithiophosphite, and the like); phosphate salts of alkali metal cations, ammonium cation, or organoammonium cations; thiophosphate salts of alkali metal cations, ammonium cation, or organoammonium cations (for example, ammonium diethyldithiophosphate, potassium diethyldithiophosphate, sodium dithiophosphatetrihydrate, and the like); phosphite salts of alkali metal cations, ammonium cation, or organoammonium cations (for example, disodium hydrogenphosphite pentahydrate and the like); hypophosphite salts of alkali metal cations, ammonium cation, or organoammonium cations (for example, sodium hypophosphite hydrate, potassium hypophosphite, ammonium hypophosphite, ethylpiperidiniumhypophosphite, tetrabutylammonium hypophosphite, and the like); phosphorus oxides (for example, $P_2O_5$ and the like); phosphorus halides and/or oxyhalides (for example, $POCl_3$, $PCl_5$, $PCl_3$, $POBr_3$, $PBr_5$, $PBr_3$, difluorophosphoric acid, fluorophosphoric acid, and the like); phosphorus sulfides (for example, $P_2S_5$, $P_2S_3$, $P_4S_3$, and the like); phosphorus halosulfides (for example, $PSCl_3$, $PSBr_3$, and the like); polyphosphoric acid; polyphosphoric acid esters; polyphosphate salts of alkali metal cations, ammonium cation, or organoammonium cations; and the like; and combinations thereof.

Preferred phosphate anion sources include phosphoric acid, phosphoric acid esters, organoammonium phosphate salts, and combinations thereof (more preferably, phosphoric acid, organoammonium phosphate salts, and combinations thereof; most preferably, phosphoric acid).

Useful phosphoric acid esters include alkylphosphates, and the like, and combinations thereof. Representative examples of useful alkylphosphates include mono-, di-, and trialkylphosphates comprising alkyl moieties having from one to about 12 carbon atoms such as methylphosphate, ethylphosphate, propylphosphate, butylphosphate, pentylphosphate, hexylphosphate, dimethylphosphate, diethylphosphate, dipropylphosphate, dibutylphosphate, dipentylphosphate, dihexylphosphate, di-2-ethylhexylphosphate, methylethylphosphate, ethylbutylphosphate, ethylpropylphosphate, trimethylphosphate, triethylphosphate, tripropylphosphate, tributylphosphate, tripentylphosphate, trihexylphosphate, tri-2-ethylhexylphosphate, ethyl dimethylphosphate, ethyl dibutylphosphate, and the like, and combinations thereof. Also useful are arylphosphates such as triphenylphosphate; alkylphosphate salts such as ammonium dilaurylphosphate; aminoethanoldihydrogenphosphate; and the like; and combinations thereof.

Preferred phosphoric acid esters include mono-, di-, and trialkylphosphates comprising alkyl moieties having from one to about four carbon atoms (for example, methylphosphate, ethylphosphate, propylphosphate, butylphosphate, dimethylphosphate, diethylphosphate, dipropylphosphate, dibutylphosphate, methylethylphosphate, ethylbutylphosphate, ethylpropylphosphate, trimethylphosphate, triethylphosphate, tripropylphosphate, tributylphosphate, ethyl dimethylphosphate, ethyl dibutylphosphate, and combinations thereof). More preferred phosphoric acid esters include mono- and dialkylphosphates comprising alkyl moieties having one to about four carbon atoms (for example, methylphosphate, ethylphosphate, propyl phosphate, butylphosphate, dimethylphosphate, diethylphosphate, dipropylphosphate, dibutylphosphate, methylethylphosphate, ethylbutylphosphate, ethylpropylphosphate, and combinations thereof). Most preferred phosphoric acid esters include monoalkylphosphates having from one to about four carbon atoms (for example, methylphosphate, ethylphosphate, propylphosphate, butylphosphate, and combinations thereof).

Useful polyphosphoric acid esters include esters of di-, tri-, tetra-, and pentaphosphoric acid and a monohydric alcohol and/or polyhydric alcohol, and the like, and combinations thereof. Representative examples of polyphosphoric acid esters include polyphosphoric acid methyl ester, polyphosphoric acid ethyl ester, polyphosphoric acid propyl ester, polyphosphoric acid butyl ester, polyphosphoric acid pentyl ester, polyphosphoric acid dimethyl ester, polyphosphoric acid diethyl ester, polyphosphoric acid dipropyl ester, polyphosphoric acid dibutyl ester, diphosphoric acid methyethyl ester, diphosphoric acid ethylbutyl ester, diphosphoric acid ethylpropyl ester, diphosphoric acid ethylhexyl ester, trialkyl esters of di-, tri-, tetra-, and penta-phosphoric acids, tetraalkyl esters of di-, tri-, tetra-, and penta-phosphoric acids, pentaalkyl esters of di-, tri-, tetra-, and penta-phosphoric acids, hexaalkyl esters of di-, tri-, tetra-, and penta-phosphoric acids, and the like, and combinations thereof. Preferred polyphosphoric acid esters include those having an ester group containing one to about four carbon atoms (for example, polyphosphoric acid methyl ester, polyphosphoric acid ethyl ester, polyphosphoric acid propyl ester, and polyphosphoric acid butyl ester), and combinations thereof.

Useful salts include alkali metal (for example, sodium or potassium) phosphates and polyphosphates, ammonium phosphates and polyphosphates, organoammonium (for example, mono-, di-, tri-, and tetraalkylammonium) phosphates and polyphosphates, and the like (including hydroxylamine phosphate), and combinations thereof. Representative examples of useful alkali metal phosphates include sodium dihydrogen phosphate (monobasic), sodium hydrogen phosphate (dibasic), trisodium phosphate (tribasic), potassium dihydrogen phosphate, lithium dihydrogenphosphate, sodium tripolyphosphate, sodium hexametaphosphate, potassium pyrophosphate, and the like, and combinations thereof.

Representative examples of useful organoammonium phosphates and polyphosphates include ethylammonium phosphate, diethylammonium phosphate, trimethylammonium phosphate, triethylammonium phosphate, tributylammonium pyrophosphate, methyltriethylammonium dibutylphosphate, pentyltriethylammonium phosphate, hexyltriethylammonium phosphate, octyltriethylammonium phosphate, dodecyltrimethylammonium phosphate, hexadecyltrimethylammonium dihydrogen phosphate, tetramethylammonium dihydrogen phosphate, tetraethylammonium dihydrogenphosphate, tetrabutylammonium phosphate, tetrahexylammonium dihydrogen phosphate, di-2-ethylhexylammonium hexafluorophosphate, tetramethylammonium hexafluorophosphate, tetraethylammonium hexafluorophosphate, tetrapropylammonium hexafluorophosphate, tetrabutylammonium hexafluorophosphate, tetrahexylammonium hexafluorophosphate, phenyltrimethylammonium hexafluorophosphate, benzyltrimethylammonium hexafluorophosphate, and the like, and combinations thereof.

Preferred organoammonium phosphate salts include pentyltriethylammonium phosphate, hexyltriethylammonium phosphate, octyltriethylammonium phosphate, dodecyltrimethylammonium phosphate, hexadecyltrimethylammonium dihydrogen phosphate, tetrahexylammonium dihydrogen phosphate, di-2-ethylhexylammonium hexafluorophosphate, tetrahexylammonium hexafluorophosphate, phenyltrimethylammonium hexafluorophosphate, benzyltrimethylammonium hexafluorophosphate, and combinations thereof (more preferably, hexyltriethylammonium phosphate, octyltriethylammonium phosphate, dodecyltrimethylammonium phosphate, tetrahexylammonium dihydrogen phosphate, di-2-ethylhexylammonium hexafluorophosphate, tetrahexylammonium hexafluorophosphate, and combinations thereof; most preferably, octyltriethylammonium phosphate, di-2-ethylhexylammonium hexafluorophosphate, and combinations thereof).

Preferred phosphate salts include organoammonium phosphates, and combinations thereof (more preferably, mono-, di-, tri-, and tetraalkylammonium phosphates, and combinations thereof; most preferably, tetraalkylammonium phosphates, and combinations thereof). Most preferably, the preferred salts comprise at least one organic moiety comprising at least about five carbon atoms.

Such phosphate anion sources can be prepared by known methods. Many of such sources (for example, phosphoric acid, alkylphosphates, and polyphosphoric acid esters) are commercially available.

Organic Base

Organic bases suitable for use in the process of the invention include those organic amines and organoammonium hydroxides that comprise at least one organic moiety comprising at least about five carbon atoms (preferably, at least about six carbon atoms; more preferably, at least about eight carbon atoms), and combinations thereof (preferably, an organic amine). The organic moiety can be linear, branched, alicyclic, aromatic, or a combination thereof (preferably, linear or branched), with the proviso that carbon atoms in a cyclic moiety count only as half their number toward the requisite minimum of five (for example, a phenyl ring counts as three carbon atoms rather than six and must be supplemented by, for example, an attached ethyl moiety). Preferably, the organic moiety comprises from about 6 to about 24 carbon atoms (more preferably, from about 6 to about 18 carbon atoms; most preferably, from about 8 to about 12 carbon atoms).

Representative examples of suitable organic amines include monoalkylamines such as hexylamine, heptylamine, octylamine, nonylamine, decylamine, dodecylamine, hexadecylamine, and octadecylamine; dialkylamines such as dihexylamine, di-n-heptylamine, di-n-octylamine, bis(2-ethylhexyl)amine, di-sec-octylamine, di-n-nonylamine, di-n-decylamine, di-n-undecylamine, di-n-tridecylamine, and dicyclooctylamine; trialkylamines such as trihexylamine, triheptylamine, triisooctylamine, trioctylamine, tridodecylamine, tris(4-methylcyclohexyl)amine, tri-n-heptylamine, trinonylamine, N,N-didecylmethylamine, N,N-dimethylcyclohexylamine, N,N-dimethyldodecylamine, N,N-dimethyloctylamine, and tris(2-ethylhexyl)amine; arylamines such as diphenylstearylamine; polyethylene glycol mono- and diamines; and the like; and combinations thereof.

Preferred organic amines include hexylamine, octylamine, decylamine, dodecylamine, hexadecylamine, dihexylamine, di-n-octylamine, bis(2-ethylhexyl)amine, di-sec-octylamine, di-n-decylamine, trihexylamine, trioctylamine, triisooctylamine, trinonylamine, tridodecylamine, tris(4-methylcyclohexyl)amine, tri-n-heptylamine, N,N-didecylmethylamine, N,N-dimethylcyclohexylamine, N,N-dimethyldodecylamine, N,N-dimethyloctylamine, tris(2-ethylhexyl)amine, and combinations thereof (more preferably, hexylamine, octylamine, decylamine, dodecylamine, dihexylamine, di-n-octylamine, bis(2-ethylhexyl)amine, di-sec-octylamine, trihexylamine, trioctylamine, triisooctylamine, tridodecylamine, tri-n-heptylamine, N,N-dimethyloctylamine, tris(2-ethylhexyl)amine, and combinations thereof; most preferably, dihexylamine, di-n-octylamine, bis(2-ethylhexyl)amine, di-sec-octylamine, trihexylamine, trioctylamine, triisooctylamine, tris(2-ethylhexyl)amine, and combinations thereof).

Representative examples of suitable organoammonium hydroxides include benzyltriethylammonium hydroxide, benzyltrimethylammonium hydroxide, hexane-1,6-bis(tributylammonium)dihydroxide, 3-(trifluoromethyl)phenyltrimethylammonium hydroxide, dodecyldimethylethylammonium hydroxide, phenyltrimethylammonium hydroxide, cetyltrimethylammonium hydroxide, triethylphenylammonium hydroxide, tetradecylammonium hydroxide, tetrabutylammonium hydroxide, tetramethylammonium hydroxide, tetraethylammonium hydroxide, tetrapropylammonium hydroxide, tetrahexylammonium hydroxide, tetraoctylammonium hydroxide, tetrapentylammonium hydroxide, methyltriethylammonium hydroxide, tetraoctadecylammonium hydroxide, dimethyldiethylammonium hydroxide, methyltripropylammonium hydroxide, tetradecyltrihexylammonium hydroxide, ethyltrimethylammonium hydroxide, tris(2-hydroxyethyl)methylammonium hydroxide, and the like, and combinations thereof.

Preferred organoammonium hydroxides include benzyltriethylammonium hydroxide, benzyltrimethylammonium hydroxide, dodecyldimethylethylammonium hydroxide, cetyltrimethylammonium hydroxide, triethylphenylammonium hydroxide, tetradecylammonium hydroxide, tetrahexylammonium hydroxide, tetraoctylammonium hydroxide, tetrapentylammonium hydroxide, tetraoctadecylammonium hydroxide, tetradecyltrihexylammonium hydroxide, and combinations thereof (more preferably, dodecyldimethylethylammonium hydroxide, cetyltrimethylammonium hydroxide, tetradecylammonium hydroxide, tetrahexylammonium hydroxide, tetraoctylammonium hydroxide, tetraoctadecylammonium hydroxide, tetradecyltrihexylammonium hydroxide, and combinations thereof; most preferably, dodecyldimethylethylammonium hydroxide, cetyltrimethylammonium hydroxide, and combinations thereof).

Such organic bases can be prepared by known methods. Many of such bases (for example, dodecyldimethylethylammonium hydroxide, cetyltrimethylammonium hydroxide, tetradecylammonium hydroxide, tetrahexylammonium hydroxide, and tetraoctylammonium hydroxide) are commercially available.

The organic bases (as well as the phosphate anion sources) can be used in neat solid or liquid form or can be used in the form of a solution in organic solvent (for example, an alkanol such as methanol). A wide range of concentrations can be useful (for example, from about 5 to about 90 weight percent in alkanol, based upon the total weight of the solution).

In a preferred embodiment of the process of the invention, the organic base can be combined with the phosphate anion source (for example, phosphoric acid), dissolved in a polar organic solvent or in at least a portion of the organosilane, and used in the form of the resulting solution. Polar organic solvents useful for dissolving the organic base include acetone, diethylether, alkanols (for example, methanol, ethanol, and isopropanol), dimethylsulfoxide (DMSO), dimethylformamide (DMF), tetrahydrofuran (THF), ethyl acetate, and the like, and mixtures thereof, with alkanols being preferred and methanol more preferred.

When the phosphate anion source is an organoammonium phosphate or polyphosphate comprising at least one organic moiety that comprises at least about five carbon atoms, the organoammonium phosphate or polyphosphate can serve as both the phosphate anion source and the organic base, without the need for addition of a separate organic base. Such dual functionality is not limited to these components, however, as other materials can simultaneously serve as more than one of the four reaction mixture components.

Organosilane

Organosilanes suitable for use in the process of the invention include those organosilanes that comprise at least one organic moiety comprising at least about six carbon atoms (preferably, at least about seven carbon atoms; more preferably, at least about eight carbon atoms), and combinations thereof. The organic moiety can be linear, branched, alicyclic, aromatic, or a combination thereof (preferably, linear or branched), with the proviso that carbon atoms in a cyclic moiety count only as half their number toward the requisite minimum of six (for example, a phenyl ring counts as three carbon atoms rather than six and must be supplemented by, for example, an attached propyl moiety). Preferably, the organic moiety comprises from about 6 to about 24 carbon atoms (more preferably, from about 7 to about 18 carbon atoms; even more preferably, from about 8 to about 12 carbon atoms). Most preferably, the organic moiety has about 8 carbon atoms (and is preferably branched).

The organosilane can function to form an organosilane surface modifier (on the surface of the metal phosphate nanoparticle) that can comprise the organosilane or a residue thereof (that is, a portion of the organosilane that remains after chemical reaction). The surface modifier can be attached or bonded to the surface of the nanoparticle by a relatively strong physical bond or by a chemical bond (for example, a covalent or ionic bond). For example, organosilane surface modifiers can be derived from alkoxysilanes through hydrolysis of the alkoxysilane and formation of a silicon-oxygen-metal or silicon-oxygen-phosphorus covalent attachment to the metal phosphate nanoparticle. Preferably, the organosilane surface modifier is derived from an organosilane selected from alkoxysilanes, halosilanes, acyloxysilanes, and aminosilanes (including primary, secondary, and tertiary amines), and combinations thereof.

A class of useful organosilanes can be represented by the following general Formula I:

$$(R)_{4-y}Si(X)_y \quad (I)$$

wherein y is an integer of 1 to 3 (preferably, 2 or 3; more preferably, 3); each R is independently selected from hydrogen and organic moieties that are linear, branched, alicyclic, aromatic, or a combination thereof (preferably, linear or branched) and that have from about 6 to about 24 carbon atoms (more preferably, from about 7 to about 18 carbon atoms; even more preferably, from about 8 to about 12 carbon atoms; most preferably, about 8 carbon atoms), with the proviso that carbon atoms in a cyclic moiety count only as half their number toward the requisite minimum of 6 carbon atoms (for example, a phenyl ring counts as three carbon atoms rather than six and must be supplemented by, for example, an attached propyl moiety), and that optionally further comprise at least one functional group selected from heterocyclic, acryloxy, methacryloxy, cyano, isocyano, cyanato, isocyanato, phosphino, amino, amido, vinyl, epoxy, glycidoxy, alkyl, carbon-carbon triple bond-containing, mercapto, siloxy, halocarbon (for example, fluorocarbon), carbon-nitrogen double bond-containing, and carbon-carbon double bond-containing groups, and combinations thereof; with the proviso that at least one R group is an organic moiety; and each X is independently selected from hydrocarbyloxy, fluoroalkanesulfonate, and alkoxy groups having from 1 to about 8 carbon atoms (preferably, 1 to about 4 carbon atoms; more preferably, 1 to about 2 carbon atoms; most preferably, 1 carbon atom), chlorine, bromine, iodine, acyloxy, amino moieties —NR'R', wherein each R' is independently selected from hydrogen and organic moieties having from 1 to about 10 carbon atoms, and combinations thereof. Preferably, at least one X is independently selected from alkoxy, acyloxy, chlorine, bromine, amino, and combinations thereof (more preferably, alkoxy, acyloxy, chlorine, amino, and combinations thereof; even more preferably, alkoxy, chlorine, amino, and combinations thereof; most preferably, alkoxy and combinations thereof). Preferably, at least one X is a hydrolyzable moiety.

When a functional group-containing organosilane is utilized, the particular functional group can be selected so as to be compatible with a material to which the resulting metal phosphate nanoparticles are to be added. Representative examples of heterocyclic functional groups include substituted and unsubstituted pyrroles, pyrazoles, imidazoles, pyrrolidines, pyridines, pyrimidines, oxazoles, thiazoles, furans, thiophenes, dithianes, isocyanurates, and the like, and combinations thereof. Representative examples of acryloxy functional groups include acryloxy, alkylacryloxy groups such as methacryloxy, and the like, and combinations thereof. Representative examples of carbon-carbon double bond-containing functional groups include alkenyl, cyclopentadienyl, styryl, phenyl, and the like, and combinations thereof.

Representative examples of useful organosilanes include phenyltrimethoxysilane; phenyltriethoxysilane; phenylethyltrimethoxysilane; diphenyldimethoxysilane; diphenyldiethoxysilane; N-[3-(triethoxysilyl)propyl]-4,5-dihydroimidazole; beta-trimethoxysilylethyl-2-pyridine; N-phenylaminopropyltrimethoxysilane; (N,N-diethyl-3-aminopropyl)trimethoxysilane; N,N-didecyl-N-methyl-N-(3-trimethoxysilylpropyl)ammonium chloride; 3-(N-styrylmethyl-2-aminoethylamino)propyltrimethoxysilane; methacryloxy-propenyltrimethoxysilane; 3-methacryloxypropyltrimethoxysilane; 3-methacryloxypropyltris(methoxyethoxy)silane; 3-cyclopentadienylpropyltriethoxysilane; 7-oct-1-enyltrimethoxysilane; 3-glycidoxypropyl-trimethoxysilane; gamma-glycidoxypropylmethyldimethoxysilane; gamma-glycidoxypropylmethyldiethoxysilane; gamma-glycidoxypropyldimethylethoxysilane; n-octyltriethoxysilane; n-octyltrimethoxysilane; isooctyltrimethoxysilane; hexyltriethoxysilane; 3-triethoxysilyl-N-(1,3-dimethyl-butyliden)propylamine; 3-acryloxypropyltrimethoxysilane; methacryloxypropylmethyldiethoxysilane; methacryloxypropylmethyldimethoxysilane; glycidoxypropylmethyldiethoxysilane; 2-(3,4 epoxycyclohexyl)-ethyltrimethoxysilane; aminophenyltrimethoxysilane; p-chloromethyl)phenyltri-n-propoxysilane; diphenylsilanediol; epoxyhexyltriethoxysilane; dococentyltrimethoxysilane; 1,4-bis(trimethoxysilylethyl)benzene; trimethoxysilyl-1,3-dithiane; n-trimethoxysilylpropylcarbamoylcaprolactam; 2-(diphenylphosphine)ethyltriethoxysilane; N,N-dioctyl-n'-triethoxysilylpropylurea; N-cyclohexylaminopropyltrimethoxysilane; 11-bromoundecyltrimethoxysilane; 1,2-bis(trimethoxysilyl)decane; bis[(3-methyldimethoxysilyl)propyl]polypropylene oxide; [(bicycloheptenyl)ethyl]trimethoxysilane; N-(6-aminohexyl)aminopropyltrimethoxysilane; [2-(3-cyclohexenyl)ethyl]trimethoxysilane; (3-cyclopentadienylpropyl)triethoxysilane; 3-(1,3-dimethylbutylidene) aminopropyltriethoxysilane; polyethyleneglycoltrialkoxysilane; n-octadecyltrichlorosilane; isooctyltrichlorsilane; 4-phenylbutyltrichlorosilane; 4-phenylbutylmethyldichlorosilane; n-dodecyltrichlorosilane; di-n-octyldichlorosilane; n-decyltrichlorsilane; n-decyldimethylchlorosilane; (cyclohexylmethyl)trichlorosilane; tridodecylbromosilane; diphenylmethylbromosilane; tert-butylmethoxyphenylbromosilane; trioctylbromosilane; 1,3-di-n-octyltetramethyldisilazane; phenylmethylbis(dimethylamino)silane; 1,3-bis(4-biphenyl)tetramethyldisilazane; 1,3-dioctadecyltetramethyldisilazane; 1,3-divinyl-1,3-diphenyl-1,3-dimethyldisilazane; and the like; and combinations thereof.

Preferred organosilanes include (N,N-diethyl-3-aminopropyl)trimethoxysilane; N, N-didecyl-N-methyl-N-(3-trimethoxysilylpropyl)ammonium chloride; 3-(N-styrylmethyl-2-aminoethylamino)propyltrimethoxysilane; methacryloxy-propenyltrimethoxysilane; 3-methacryloxypropyltrimethoxysilane; 3-cyclopentadienylpropyltriethoxysilane; 7-oct-1-enyltrimethoxysilane; 3-glycidoxypropyl-trimethoxysilane; gamma-glycidoxypropylmethyldiethoxysilane; n-octyltriethoxysilane; n-octyltrimethoxysilane; isooctyltrimethoxysilane; hexyltriethoxysilane; 3-acryloxypropyltrimethoxysilane; methacryloxypropylmethyldimethoxysilane; 2-(3,4 epoxycyclohexyl)-ethyltrimethoxysilane; p-chloromethyl)phenyltri-n-propoxysilane; epoxyhexyltriethoxysilane; dococentyltrimethoxysilane; N-cyclohexylaminopropyltrimethoxysilane; polyethyleneglycoltrimethoxysilane; n-octadecyltrichlorosilane; isooctyltrichlorsilane; 4-n-dodecyltrichlorosilane; di-n-octyldichlorosilane; n-decyltrichlorsilane; n-decyldimethylchlorosilane; (cyclohexylmethyl)trichlorosilane; trioctylbromosilane; tridodecylbromosilane; 1,3-di-n-octyltetramethyldisilazane; dioctadecyltetramethyldisilazane; and combinations thereof.

More preferred organosilanes include (N,N-didecyl-N-methyl-N-(3-trimethoxysilylpropyl)ammonium chloride; 3-methacryloxypropyltrimethoxysilane; 3-glycidoxypropyl-trimethoxysilane; gamma-glycidoxypropylmethyldiethoxysilane; n-octyltriethoxysilane; n-octyltrimethoxysilane; isooctyltrimethoxysilane; hexyltriethoxysilane; 3-acryloxypropyltrimethoxysilane; 2-(3,4-epoxycyclohexyl)-ethyltrimethoxysilane; epoxyhexyltriethoxysilane; N-cyclohexylaminopropyltrimethoxysilane; polyethyleneglycoltrimethoxysilane; isooctyltrichlorosilane; n-decyltrichlorosilane; (cyclohexylmethyl)trichlorosilane; trioctylbromosilane; 1,3-di-n-octyltetramethyldisilazane; and combinations thereof.

Most preferred organosilanes include n-octyltrimethoxysilane; isooctyltrimethoxysilane; hexyltriethoxysilane; polyethyleneglycoltrimethoxysilane; and combinations thereof.

Such organosilanes can be prepared by known methods (for example, from organosilane precursor compounds such as corresponding halosilanes or hydrosilanes). Many of such organosilanes (for example, 3-methacryloxypropyltrimethoxysilane; 3-glycidoxypropyltrimethoxysilane; n-octyltrimethoxysilane; isooctyltrimethoxysilane; hexyltriethoxysilane; 3-acryloxypropyltrimethoxysilane; 2-(3,4-epoxycyclohexyl)-ethyltrimethoxysilane; N-cyclohexylaminopropyltrimethoxysilane; polyethyleneglycoltrimethoxysilane; isooctyltrichlorosilane; and 1,3-di-n-octyltetramethyldisilazane) are commercially available.

Solvents

Solvents can be used in carrying out the process of the invention, if desired. Suitable solvents include those in which the various metal phosphate precursors or reaction mixture components can be substantially soluble or dispersible. Most preferably, the solvent will be capable of dissolving the reactants and products of the process, while keeping the desired metal phosphate nanoparticles well-dispersed.

Useful solvents for dissolving or dispersing more polar components such as the organic base and/or the phosphate anion source include polar organic solvents (for example, dimethylsulfoxide (DMSO), dimethylformamide (DMF), formamide, acetonitrile, acetone, methylethylketone (MEK), alkanols (for example, methanol, ethanol, isopropanol, 2-methoxyethanol, 1-methoxy-2-propanol, 1-methoxy-2-methyl-2-propanol, ethylene glycol, and the like, and combinations thereof), N-methylpyrrolidinone (NMP), and the like, and combinations thereof. Preferred polar organic solvents can include acetonitrile, acetone, MEK, alkanols, and combinations thereof, due to their relatively high polarities and relatively low boiling points. More preferred polar organic solvents can include alkanols (most preferably, methanol, ethanol, and combinations thereof), however, due to the generally good solubility of reaction byproducts in these solvents and the ease of solvent removal (along with the byproducts) during purification.

Useful solvents for dissolving or dispersing less polar components such as the long-chain organosilanes include non-polar organic solvents such as alkanes (for example, hexane, heptane, octane, and the like, and combinations thereof) and aromatic hydrocarbons (for example, toluene, benzene, xylene, and the like, and combinations thereof), as well as more polar solvents such as esters (for example, ethyl acetate and the like, and combinations thereof), ethers (for example, tetrahydrofuran (THF), diethylether, and the like, and combinations thereof), and halocarbons (for example, carbon tetrachloride and the like, and combinations thereof), and the like, and combinations thereof. Preferred non-polar organic solvents include hexane, heptane, octane, toluene, and combinations thereof, due to their boiling points.

Mixtures of the polar and non-polar solvents can advantageously be utilized to facilitate separation of the resulting metal phosphate nanoparticles from reaction byproducts. Water in relatively small amounts can speed the kinetics of growth of the metal phosphate nanoparticles and/or facilitate hydrolysis of the organosilane surface modifier, but the presence of water in relatively larger amounts (for example, a water to metal ratio of greater than about 25) can cause nanoparticle agglomeration and/or loss of substantially spherical morphology.

Process

The process of the invention can be carried out by combining at least one metal cation source, at least one phosphate anion source, at least one organic base comprising at least one organic moiety comprising at least about five carbon atoms, and at least one organosilane comprising at least one organic moiety comprising at least about six carbon atoms (preferably, in at least one solvent). Generally, any order and manner of combination of the four reaction mixture components can be utilized, although it can sometimes be preferable to dissolve or disperse one or more components (for example, the phosphate anion source and the organic base) separately in solvent prior to combination with the other components.

Depending upon the specific chemical natures of the selected components and the amount of water present, certain orders and manners of combination can assist in minimizing agglomeration and enabling the formation of nanoparticles. For example, it can be preferable (for example, when using relatively more reactive phosphate anion sources such as phosphoric acid) to separately form a mixture of the phosphate anion source and the organic base and a mixture of the metal cation source and the organosilane. These two mixtures can then be combined.

The metal cation source and the phosphate anion source can be combined in generally stoichiometric amounts, based upon the moles of metal cation and the moles of phosphate anion. For example, these components can be combined in amounts such that the metal to phosphorus molar ratio ranges from about 0.8/n to about 6.0/n, where n is the valency of the metal. Preferably, the molar ratio ranges from about 1.0/n to about 4.0/n (more preferably, from about 1.4/n to about 3.4/n).

The metal cation source (for example, a metal salt comprising a metal cation and counteranion(s)) and the organic base can be combined in generally stoichiometric amounts, based upon the moles of basic groups and the moles of counteranion. For example, these components can be combined in amounts such that the organic base to metal molar ratio ranges from about 0.5 n/b to about 3.0 n/b, where n is the valency of the metal and b is the number of basic groups per mole of organic base. Preferably, the molar ratio ranges from about 0.6 n/b to about 2.0 n/b (more preferably, from about 0.7 n/b to about 1.5 n/b).

The metal cation source and the organosilane can be combined in amounts such that the molar ratio of metal to silicon ranges from about 0.1 to about 20 (preferably, from about 0.2 to about 15; more preferably, from about 0.3 to about 10). If desired, however, the organosilane can be used in larger amounts, so as to function as a reaction solvent. Generally less than 100 percent of the combined organosilane attaches (for example, physically or chemically) to the metal phosphate nanoparticles to provide surface modification.

Mechanical agitation or stirring can be used, if desired, to facilitate mixing. Optionally, heating can be used to facilitate dissolution, reaction, and/or primary particle size growth. The reaction mixture components can be combined in a pressure vessel, if desired (for example, this can be useful for reactions carried out at temperatures above the boiling point of a selected solvent). An inert atmosphere (for example, nitrogen) can optionally be utilized (for example, to minimize the presence of moisture or air).

To influence, for example, the morphology, magnetic properties, conductivity, light absorption or emission characteristics, and/or the crystallinity of the resulting nanoparticles, various compounds (foreign ions) can be added before, during, or after nanoparticle precipitation. Preferred additive compounds include 2nd-5th main group and transition metal compounds (more preferably, magnesium, strontium, barium, aluminum, indium, tin, lead, antimony, bismuth, titanium, vanadium, chromium, manganese, iron, cobalt, nickel, zinc, yttrium, zirconium, niobium, molybdenum, cadmium, hafnium, tantalum, and tungsten compounds, and combinations thereof; most preferably, magnesium, strontium, aluminum, tin, antimony, titanium, manganese, iron, zinc, yttrium, zirconium, niobium, and tantalum compounds, and combinations thereof) including lanthanide compounds (more preferably, europium, terbium, dysprosium, samarium, erbium, praseodymium, and cerium compounds, and combinations thereof; most preferably, cerium, europium, terbium, and dysprosium compounds, and combinations thereof). Such additive compounds preferably can be added to the reaction mixture in dissolved form and/or preferably can be used in an amount from about 0.01 to about 20 mole percent, based on the total number of moles of metal (present, for example, in the form of metal phosphate).

Other common additives (for example, dyes, pigments, catalysts, and the like) can also be utilized. Monomer(s), oligomer(s), and/or polymer(s) of various types can be present in the reaction mixture (for example, in order to form a polymeric composite comprising the resulting metal phosphate nanoparticles).

The resulting nanoparticles can be isolated (for example, from a resulting sol) and/or purified by using standard techniques such as decantation (for example, following centrifugation or settling optionally induced by cosolvent addition), filtration, rotary evaporation for solvent removal, dialysis, diafiltration, and the like, and combinations thereof. The characteristics of the resulting product can be evaluated by ultraviolet-visible spectroscopy (absorption characteristics), X-ray diffraction (crystalline particle size, crystalline phase, and particle size distribution), transmission electron microscopy (particle sizes, crystalline phase, and particle size distributions), and dynamic light scattering (degree of agglomeration).

Upon solvent removal (for example, by rotary evaporation, air or oven drying, centrifugation and decantation, a change in solvent polarity followed by gravitational settling and decantation, or the like), the resulting nanoparticles can be in the form of a powder or gel that can be re-dispersed in solvent (for example, a polar or a non-polar solvent, depending upon the specific chemical nature of the organosilane). The resulting nanoparticles can range in average primary particle diameter from about 1 nm to about 50 nm or more (preferably, from about 1 nm to about 30 nm; more preferably, from about 1 nm to about 20 nm; even more preferably, from about 1 nm to about 15 nm; most preferably, from about 2 nm to about 10 nm), where any lower limit can be paired with any upper limit of the size ranges as explained above.

The nanoparticles can be used in various different applications (for example, calcium phosphate nanoparticles can be used in various pharmaceutical, medical, and dental applications). Preferred embodiments of the process of the invention can provide substantially spherical nanoparticles (for example, substantially spherical calcium phosphate nanoparticles useful in inhalable aerosol drug delivery systems).

EXAMPLES

Objects and advantages of this invention are further illustrated by the following examples, but the particular materials and amounts thereof recited in these examples, as well as other conditions and details, should not be construed to unduly limit this invention. These examples are merely for illustrative purposes only and are not meant to be limiting on the scope of the appended claims.

All parts, percentages, ratios, etc. in the examples and the rest of the specification are by weight, unless noted otherwise. Solvents and other reagents used were obtained from Sigma-Aldrich Chemical Company, St. Louis, Mo., unless otherwise noted. All chemicals and reagents were used without further purification unless noted otherwise.

Materials

Calcium chloride hexahydrate (98 percent (%) purity), manganese (II) chloride tetrahydrate (99.99% purity), crystalline phosphoric acid (99% purity; Fluka), and methyltrimethoxysilane (98% purity) were obtained from Sigma-Aldrich Chemical Company, St. Louis, Mo.

Zinc chloride (anhydrous; 99.99% purity), europium (III) chloride hexahydrate (99.9% purity), terbium (III) chloride hexahydrate (99.9% purity), isobutyltrimethoxysilane (97% purity), n-octyltrimethoxysilane (97% purity), and tri-n-octylamine (98% purity) were purchased from Alfa Aesar, Ward Hill, Mass.

Isooctyltrimethoxysilane (greater than 95% purity) was purchased from Gelest Inc., Morrisville, Pa.

n-Octadecyltrimethoxysilane (95% purity) was purchased from TCI America, Portland, Oreg.

Magnesium chloride hexahydrate (99% purity) was purchased from EM Science, Gibbstown, N.J.

Cobalt chloride hexahydrate (99.9% purity) was purchased from Fisher Scientific, Fairlawn, N.J.

Methanol (ACS grade; BDH) and ethanol (200 proof; absolute) were obtained from VWR, West Chester, Pa. and AAPER, Shelbyville, Ky., respectively.

Heptane, xylenes, hexanes, and toluene were purchased from EMD Chemicals, Gibbstown, N.J.

Test Methods

X-ray Diffraction (XRD)

Reflection geometry X-ray diffraction data were collected using a Bruker™ D8 Advance diffractometer (Bruker-AXS, Madison, Wis., USA), copper $K_\alpha$ radiation, and Vantec™ detector registry of the scattered radiation. The diffractometer was fitted with variable incident beam slits and fixed diffracted beam slits. The survey scan was conducted in coupled continuous mode from 5 to 80 degrees (2θ) using a 0.015 degree step size and 2 second dwell time. X-ray generator settings of 40 kV and 40 mA were employed. Tested samples were first milled to produce a fine powder and applied as dry powders to specimen holders containing glass inserts.

Particle Size Determination in Dispersion

Particle size distribution was measured by Dynamic Light Scattering (DLS) using a Malvern Instruments Zetasizer-NanoZS™, Model No. ZEN3600 particle size analyzer (available from Malvern Instruments, Malvern, U.K.). 10 weight percent (% w/w) dispersions of sample compositions were prepared in hexane for DLS measurements. A small (50 mg) aliquot was taken from the dispersion and diluted with 2.5 g of hexane. The resulting diluted sample was mixed well and then transferred to a glass cuvette. Light scattering data was recorded with the sample temperature set at 25° C. For all measurements, the solvent (hexane) and the dispersions were filtered using 0.2 micrometer (μ) polytetrafluoroethylene (PTFE) filter. For transforming autocorrelation function into particle size, standard values for the viscosity ($0.294\times10^{-3}$ Pa·s; 0.294 cp) and refractive index (1.375) of hexane and the viscosity ($0.39\times10^{-3}$ Pa·s; 0.39 cp) and refractive index (1.39) of heptane at 25° C. were used. Refractive index values of 1.63 for calcium phosphate, 1.51 for magnesium phosphate, 1.59 for zinc phosphate, and 1.61 for cobalt phosphate were used. The reported Z-average diameter (average agglomerated particle diameter, d, in nm) was based upon an intensity weighted distribution. Particle size distribution was also measured as a function of time in order to study the stability of the dispersion and the agglomeration of the particles by collecting the DLS data over a period of 18 hours with a time delay of 2 hours between measurements. All results are reported in terms of particle size, d (nm), and polydispersity index (PdI).

Transmission Electron Microscopy (TEM)

Samples were prepared by placing a drop of a 2 weight percent heptane or hexane colloidal suspension onto the carbon side of a carbon grid sample holder (type 01801, from Ted Pella Inc., Redding Calif., USA). Excess solvent was wicked from the sample holder, and the remaining slurry was air dried for 5 minutes before use. The samples were examined in a JEOL™ JSM 200CX transmission electron microscope (TEM) (JEOL, Tokyo, Japan) at 200 KV. Pictures of the particulate material were imaged at 50 and 100Kx and Selected Area Diffraction (SAD) was used to determine crystal type and size. Some dark field imaging was conducted to illuminate the crystal phases and again determine crystal size. The images and SAD patterns were captured and digitized for image analysis.

Examples 1-16 and Comparative Examples C1-C5

In a 3-neck round bottom reaction flask connected to a condenser via a Dean-Stark receiver, Component Mixture 1 was mixed with Component Mixture 2 as specified in Table 1 below, and the resulting reaction mixture was stirred at Reaction Condition A of Table 1 in a stream of nitrogen until one cloudy and one clear layer were observed in the reaction flask. At this temperature, Component Mixture 3 was added as specified in Table 1. The reaction mixture was then maintained under Reaction Condition 2 as indicated in Table 1. To the warm reaction mixture was added a four-fold excess of methanol (by volume) leading to the precipitation of white solid. Centrifugation of the mixture, followed by subsequent washes of the solid with ethanol, provided clean powder of metal phosphate. The powder was dried in an oven (200° C.) for 15 minutes to give dried metal phosphate powder. The redispersibility characteristics of the dried powder were determined, as shown in Table 1. The dried powder was further characterized by XRD, DLS, and TEM as appropriate, and the results are reported in Table 1.

Generally, the dried powder was easily redispersed in solvents such as toluene, xylene, hexane, and heptane at ambient temperature to yield optically clear and stable dispersions. In many cases, the dried powder was stored in a vial for several months and then redispersed in the above solvents to yield optically clear and stable dispersions.

In Example 1, the redispersibility characteristics were somewhat different. To the warm reaction mixture of Example 1 was added 160 g of methanol, and the mixture was centrifuged at 3500 rpm (revolutions per minute) for 10 minutes. The resulting supernatant was discarded, another 160 g of methanol was added to the resulting gel-like precipitate, and the resulting mixture was centrifuged again. 35 g of hexane was added to precipitate that was isolated by removing the resulting supernatant, and the resulting mixture was centrifuged to remove any residues which settled at the bottom. The resulting supernatant was washed with 320 g methanol and 160 g ethanol. The solvent was removed using a rotary evaporator to provide a sticky gel, which on drying yielded a glassy solid. This glassy solid could not be redispersed to give a stable dispersion in heptane, hexane, or xylene, but the sticky gel was redispersed in heptane, hexane, and xylene to give optically clear and stable dispersions.

For Examples 14 and 15, the resulting dried powders were stored for 8 weeks, dispersions of each were prepared, and the particle size distributions of each were then measured by DLS as a function of time. The resulting data (reported in Table 2) showed essentially no change in Z-average particle diameter with progression of time and, when averaged, showed the mean average particle sizes reported in Table 3. This data indicated that there had been essentially no loss of redispersibility upon storage.

TABLE 1

| Example No. | Component Mixture 1 | Component Mixture 2 | Reaction Condition A | Component Mixture 3 |
|---|---|---|---|---|
| C1 | Calcium Chloride Hexahydrate (4.4 g) | Tri-n-octylamine (7.6 g) | 130° C. for 20 minutes | Phosphoric acid (2 g) & Tri-n-octylamine (7 g) in methyl alcohol (2 g) |
| C2 | Calcium Chloride Hexahydrate (4 g) | Isooctyltrimethoxysilane (12.84 g) | 130° C. until one cloudy and one clear layer observed | Phosphoric acid (1.8 g) in methyl alcohol (6 g) |
| C3 | Calcium Chloride Hexahydrate (2.2 g) | Isooctyltrimethoxysilane (7 g) | 130° C. until one cloudy and one clear layer observed | Phosphoric acid (1 g) & Tri-n-butylamine (7 g) in methyl alcohol (5 g) |
| C4 | Calcium Chloride Hexahydrate (4 g) | Methyltrimethoxysilane (7.45 g) | 130° C. until one cloudy and one clear layer observed | Phosphoric acid (1.8 g) & Tri-n-octylamine (12.9 g) in methyl alcohol (6 g) |
| C5 | Calcium Chloride Hexahydrate (4.4 g) | Isobutyltrimethoxysilane (12.5 g) | 130° C. until one cloudy and one clear layer observed | Phosphoric acid (2 g) & Tri-n-octylamine (14.2 g) in methyl alcohol (g) |
| 1 | Calcium Chloride Hexahydrate (4 g) | n-Octyltrimethoxysilane (12.8 g) | 130° C. until one cloudy and one clear layer observed | Phosphoric acid 1.8 g) & Tri-n-octylamine (12.9 g) in methyl alcohol (6 g) |
| 2 | Calcium Chloride Hexahydrate (19.7 g) | Isooctyltrimethoxysilane (50 g) | 130° C. until one cloudy and one clear layer observed | Phosphoric acid (8.8 g) & Tri-n-octylamine (63.6 g) in Isooctyltrimethoxysilane (50 g) |
| 3 | Calcium Chloride Hexahydrate (13.8 g) | Isooctyltrimethoxysilane (35 g) | 130° C. until one cloudy and one clear layer observed | Phosphoric acid (6.2 g) & Tri-n-octylamine (44.6 g) in Isooctyltrimethoxysilane (35 g) |
| 4 | Calcium Chloride Hexahydrate (4 g) | Isooctyltrimethoxysilane (10.2 g) | 130° C. until one cloudy and one clear layer observed | Phosphoric acid (1.8 g) & Tri-n-octylamine (12.9 g) in Isooctyltrimethoxysilane (10.2 g) |
| 5 | Calcium Chloride Hexahydrate (4 g) | Isooctyltrimethoxysilane (10.1 g) | 130° C. until one cloudy and one clear layer observed | Phosphoric acid (1.2 g) & Tri-n-octylamine (12.9 g) in Isooctyltrimethoxysilane (10.1 g) |
| 6 | Calcium Chloride Hexahydrate (4 g) | Isooctyltrimethoxysilane (10.2 g) | 130° C. until one cloudy and one clear layer observed | Phosphoric acid (1.8 g) & Tri-n-octylamine (12.9 g) in methyl alcohol (2 g) |
| 7 | Calcium Chloride Hexahydrate (4.4 g) | Isooctyltrimethoxysilane (14 g) | 130° C. until one cloudy and one clear layer observed | Phosphoric acid (2 g), Tri-n-butyl amine (2 g) & Tri-n-octylamine (10.4 g) in methyl alcohol (5 g) |

TABLE 1-continued

| | | | | |
|---|---|---|---|---|
| 8 | Isooctyltrimethoxysilane (12.8 g) | Phosphoric acid (1.8 g) & Tri-n-octylamine (12.9 g) | 110° C. for 10 minutes | Calcium Chloride Hexahydrate (4 g) |
| 9 | Calcium Chloride Hexahydrate (2.5 g) | Octadecyltrimethoxysilane (8.2 g) | 130° C. until one cloudy and one clear layer observed | Phosphoric acid (0.9 g), Tri-n-octylamine (6.5 g) & n-Octadecyltrimethoxysilane (8.2 g) |
| 10 | Magnesium Chloride Hexahydrate (3.7 g) | Isooctyltrimethoxysilane (10.1 g) | 130° C. until one cloudy and one clear layer observed | Phosphoric acid (1.8 g) & Tri-n-octylamine (12.9 g) in Isooctyltrimethoxysilane (10.1 g). |
| 11 | Calcium Chloride Hexahydrate (3.8 g) and $EuCl_3 \cdot 6H_2O$ (0.33 g) | Isooctyltrimethoxysilane (10.8 g) | 130° C. until one cloudy and one clear layer observed | Phosphoric acid (1.8 g) & Tri-n-octylamine (12.9 g) in Isooctyltrimethoxysilane (10.8 g) |
| 12 | Calcium Chloride Hexahydrate (3.8 g) and $TbCl_3 \cdot 6H_2O$ (0.34 g) | Isooctyltrimethoxysilane (10.2 g) | 130° C. until one cloudy and one clear layer observed | Phosphoric acid (1.8 g) & Tri-n-octylamine (12.9 g) in Isooctyltrimethoxysilane (10.2 g). |
| 13 | Zinc Chloride (2.7 g) in water (2.2 g) | Isooctyltrimethoxysilane (14 g) | 130° C. until one cloudy and one clear layer observed | Phosphoric acid (1.9 g) & Tri-n-octylamine (14.1 g) in methyl alcohol (2 g) |
| 14 | Cobalt (II) Chloride (4.7 g) | Isooctyltrimethoxysilane (14 g) | 130° C. until one cloudy and one clear layer observed | Phosphoric acid (1.9 g) & Tri-n-octylamine (14.1 g) in methyl alcohol (2 g) |
| 15 | Zinc Chloride (4.9 g) and Manganese (II) Chloride (0.79 g) in water (4 g) | Isooctyltrimethoxysilane (28.1 g) | 130° C. until one cloudy and one clear layer observed | Phosphoric acid (3.9 g) & Tri-n-octylamine (28.2 g) in methyl alcohol (5 g) |
| 16 | Calcium Chloride Hexahydrate (20 g) | Isooctyltrimethoxysilane (64.2 g) | 120° C. until one cloudy and one clear layer observed | Phosphoric acid (9.0 g) & Tri-n-octylamine (64.6 g) in methyl alcohol (16 g) |

| Example No. | Reaction Condition B | d (nm) | PdI | XRD | TEM | Redispersibility |
|---|---|---|---|---|---|---|
| C1 | Added heptane (35 g); 110° C. for 2 hours | | | | | No redispersion |
| C2 | Added heptane (35 g); 110° C. for 1 hour | | | | | No redispersion |
| C3 | Added heptane (20 g); 110° C. for 0.5 hour | | | | | No redispersion |
| C4 | Added heptane (35 g); 100° C. for 0.5 hour | | | | | No redispersion |
| C5 | Added heptane (30 g); 110° C. for 15 minutes | | | Broad peaks; nanosized material | | Redispersible but unstable |
| 1 | Added heptane (35 g); 110° C. for 2.5 hours | 40.84 | 0.259 | | | Redisperible from gel only (2 months) prior to complete drying |
| 2 | 110° C. for 3 hours | 21.93 | 0.218 | Broad peaks; nanosized material | | Redispersible even after storage as powder for 5 months |
| 3 | 110° C. for 3 hours | 27.43 | 0.25 | Broad peaks; nanosized material | Unagglomerated; primary particle size 2-10 nm | Redispersible even after storage as powder for 5 months |
| 4 | 110° C. for 3 hours | 38.69 | 0.085 | Broad peaks; nanosized material | Unagglomerated; primary particle size 2-8 nm (average = 4.7 nm based on 89 particles) | Redispersible even after storage as powder for 3 months |
| 5 | 110° C. for 2 hours | 61.31 | 0.104 | | | Redispersible even after storage as powder for 3 months |
| 6 | Added heptane (33 g); 110° C. for 15 hours | 47.66 | 0.453 | — | | Redispersible even after storage as powder for 3 months |

TABLE 1-continued

| | | | | | | |
|---|---|---|---|---|---|---|
| 7 | Added heptane (20 g); 110° C. for 2 hours | 23.79 | 0.448 | Broad peaks; nanosized material | | Redispersible even after storage as powder for 2 weeks |
| 8 | Added n-octane (50 g); 110° C. for 15 hours | — | — | Broad peaks; nanosized material | | Redispersible even after storage as powder for 3 weeks |
| 9 | Added heptane (26.6 g); 110° C. for 2 hours | — | — | | | Redispersible even after storage as powder for 3 months |
| 10 | 110° C. for 2 hours | 92.59 | 0.15 | Broad peaks; nanosized material | Unagglomerated; primary particle size 2-15 nm | Redispersible even after storage as powder for 3 months |
| 11 | 110° C. for 2 hours | 31.9 | 0.328 | Broad peaks; nanosized material | | Redispersible even after storage as powder for 3 months |
| 12 | 110° C. for 2 hours | 69.29 | 0.176 | Broad peaks; nanosized material | — | Redispersible even after storage as powder for 3 months |
| 13 | Added heptane (75 g); 110° C. for 2 hours | 57.82 | 0.403 | Broad peaks; nanosized material | Unagglomerated; primary particle size 2-10 nm | Redispersible even after storage as powder for 2 months |
| 14 | Added heptane (75 g); 110° C. for 2 hours | 36.55 | 0.398 | Broad peaks; nanosized material | Unagglomerated; primary particle size 2-10 nm | Redispersible even after storage for 2 months as powder |
| 15 | Added heptane (75 g); 110° C. for 2 hours | 75.87 | 0.186 | Broad peaks; nanosized material | | Redispersible even after storage for 2 months as powder |
| 16 | Added heptane (140 g); 110° C. for 1.5 hours | — | — | Broad peaks; nanosized material | | Redispersible even after storage for 2 months as powder |

TABLE 2

| Time (hours) | Example 14 d (nm) | Example 14 PdI | Example 15 d (nm) | Example 15 PdI |
|---|---|---|---|---|
| 0 | 34.45 | 0.309 | 62.62 | 0.214 |
| 2 | 34.35 | 0.297 | 58.51 | 0.175 |
| 4 | 33.96 | 0.297 | 59.23 | 0.171 |
| 6 | 34.31 | 0.304 | 59.08 | 0.199 |
| 8 | 34.49 | 0.303 | 59.85 | 0.213 |
| 10 | 34.35 | 0.302 | 59.56 | 0.207 |
| 12 | 34.53 | 0.290 | 60.62 | 0.211 |
| 14 | 34.42 | 0.299 | 59.37 | 0.198 |
| 16 | 34.31 | 0.300 | 58.66 | 0.187 |
| 18 | 34.64 | 0.303 | 59.85 | 0.199 |

TABLE 3

| Example No. | Mean d (nm) | Standard Deviation | Mean PdI | Standard Deviation |
|---|---|---|---|---|
| 14 | 34.38 | 0.1817 | 0.301 | 0.005 |
| 15 | 59.74 | 1.187 | 0.197 | 0.015 |

The referenced descriptions contained in the patents, patent documents, and publications cited herein are incorporated by reference in their entirety as if each were individually incorporated. Various unforeseeable modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only, with the scope of the invention intended to be limited only by the claims set forth herein as follows:

We claim:

1. A process comprising (a) combining (1) at least one metal cation source, (2) at least one phosphate anion source, (3) at least one organic base comprising at least one organic moiety comprising at least five carbon atoms, and (4) at least one organosilane comprising at least one organic moiety comprising at least six carbon atoms; and (b) allowing said metal cation source and said phosphate anion source to react in the presence of said organic base and said organosilane.

2. The process of claim 1, wherein said metal cation source is a metal salt comprising at least one metal cation and at least one anion that is capable of being displaced by phosphate anion.

3. The process of claim 2, wherein said metal cation is selected from cations of transition metals, alkaline earth metals, alkali metals, post-transition metals, and combinations thereof and/or wherein said anion is selected from halide, nitrate, acetate, carbonate, alkanoate, alkoxide, lactate, oleate, acetylacetonate, sulfate, thiosulfate, sulfonate, bromate, perchlorate, tribromoacetate, trichloroacetate, trifluoroacetate, sulfide, hydroxide, oxide, and combinations thereof.

4. The process of claim 1, wherein the metal cation of said metal cation source is selected from divalent metal cations and combinations thereof.

5. The process of claim 1, wherein the metal cation of said metal cation source is selected from alkaline earth metal cations and combinations thereof.

6. The process of claim 1, wherein the metal cation of said metal cation source is a calcium cation.

7. The process of claim 1, wherein said phosphate anion source is selected from phosphorus-containing compounds that are capable of providing phosphate anion either directly or upon dissolution, dispersion, oxidation, or hydrolysis.

8. The process of claim 1, wherein said phosphate anion source is selected from phosphoric acid; phosphorous acid; hypophosphorous acid; thiophosphoric acid; phosphoric acid esters; thiophosphoric acid esters; phosphite esters; thiophosphite esters; phosphate salts of alkali metal cations, ammonium cation, or organoammonium cations; thiophosphate salts of alkali metal cations, ammonium cation, or organoammonium cations; phosphite salts of alkali metal cations, ammonium cation, or organoammonium cations; hypophosphite salts of alkali metal cations, ammonium cation, or organoammonium cations; phosphorus oxides; phosphorus halides; phosphorus oxyhalides; phosphorus sulfides; phosphorus halosulfides; polyphosphoric acid; polyphosphoric acid esters; polyphosphate salts of alkali metal cations, ammonium cation, or organoammonium cations; and combinations thereof.

9. The process of claim 8, wherein said phosphate anion source is selected from phosphoric acid, phosphoric acid esters, organoammonium phosphate salts, and combinations thereof.

10. The process of claim 9, wherein said phosphate anion source is selected from phosphoric acid, organoammonium phosphate salts, and combinations thereof.

11. The process of claim 1, wherein said phosphate anion source is phosphoric acid.

12. The process of claim 1, wherein said organic base comprises at least one organic moiety having from 6 to 24 carbon atoms; and/or wherein said organic base is selected from organic amines, organoammonium hydroxides, and combinations thereof.

13. The process of claim 1, wherein said organosilane comprises at least one organic moiety having from 6 to 24 carbon atoms.

14. The process of claim 1, wherein said organosilane is selected from those represented by the following general Formula I:

$$(R)_{4-y}Si(X)_y \qquad (I)$$

wherein y is an integer of 1 to 3; each R is independently selected from hydrogen and organic moieties that are linear, branched, alicyclic, aromatic, or a combination thereof and that have from 6 to 24 carbon atoms, with the proviso that carbon atoms in a cyclic moiety count only as half their number toward the requisite minimum of 6 carbon atoms, and that optionally further comprise at least one functional group selected from heterocyclic, acryloxy, methacryloxy, cyano, isocyano, cyanato, isocyanato, phosphino, amino, amido, vinyl, epoxy, glycidoxy, alkyl, carbon-carbon triple bond-containing, mercapto, siloxy, halocarbon, carbon-nitrogen double bond-containing, and carbon-carbon double bond-containing groups, and combinations thereof; with the proviso that at least one said R group is a said organic moiety; and each X is independently selected from hydrocarbyloxy, fluoroalkanesulfonate, and alkoxy groups having from 1 to 8 carbon atoms, chlorine, bromine, iodine, acyloxy, amino moieties —NR'R', wherein each R' is independently selected from hydrogen and organic moieties having from 1 to 10 carbon atoms, and combinations thereof.

15. The process of claim 14, wherein said y is 2 or 3; wherein said organic moiety of said R is linear, branched, or a combination thereof; wherein said organic moiety of said R has from 7 to 18 carbon atoms; and/or wherein at least one said X is independently selected from alkoxy, acyloxy, chlorine, bromine, amino, and combinations thereof.

16. The process of claim 1, wherein said organosilane is a trialkoxysilane.

17. The process of claim 1, wherein said combining comprises forming a first mixture of said phosphate anion source and said organic base, forming a second mixture of said metal cation source and said organosilane, and then combining said first mixture and said second mixture.

18. The process of claim 1, wherein said process further comprises isolating metal phosphate nanoparticles resulting from said reaction.

19. A process comprising (a) combining (1) at least one metal halide salt, (2) phosphoric acid, (3) at least one trialkylamine comprising at least one linear or branched alkyl moiety comprising at least six carbon atoms, and (4) at least one trialkoxysilane comprising at least one linear or branched organic moiety comprising at least seven carbon atoms; and (b) allowing said metal halide salt and said phosphoric acid to react in the presence of said trialkylamine and said trialkoxysilane.

20. The process of claim 19, wherein the metal of said metal halide salt is selected from alkaline earth metals, transition metals, and combinations thereof; wherein said organic moieties have from 8 to 18 carbon atoms; and/or wherein said combining comprises forming a first mixture of said phosphoric acid and said trialkylamine, forming a second mixture of said metal halide salt and said trialkoxysilane, and then combining said first mixture and said second mixture.

* * * * *

UNITED STATES PATENT AND TRADEMARK OFFICE
CERTIFICATE OF CORRECTION

PATENT NO. : 8,404,876 B2
APPLICATION NO. : 12/989452
DATED : March 26, 2013
INVENTOR(S) : Neeraj Sharma It is certified that error appears in the above-identified patent and that said Letters Patent is hereby corrected as shown below:

On the Title Page

Column 2,
Line 24, First page, (56) References Cited, OTHER PUBLICATIONS, delete "Nanoparticies" and insert --Nanoparticles--, therefor.

Column 2,
Line 30, First page, (56) References Cited, OTHER PUBLICATIONS, delete "nanoparticies" and insert --nanoparticles--, therefor.

Column 2,
Line 11, Page 2, (56) References Cited, OTHER PUBLICATIONS, delete "Ostheoporosis" and insert --Osteoporosis--, therefor.

In the Specification

Column 5,
Line 2, delete "thereof" and insert --thereof;--, therefor.

Column 7,
Line 20, delete "methyethyl" and insert --methylethyl--, therefor.

Column 12,
Line 5, delete "n-decyltrichlorsilane;" and insert --n-decyltrichlorosilane;--, therefor.

Column 12,
Line 33, delete "n-decyltrichlorsilane;" and insert --n-decyltrichlorosilane;--, therefor.

Signed and Sealed this
First Day of July, 2014

Michelle K. Lee
*Deputy Director of the United States Patent and Trademark Office*

CERTIFICATE OF CORRECTION (continued)
U.S. Pat. No. 8,404,876 B2

Column 13,
Line 14, delete "N-methylpyrrolidinone" and insert --N-methyl pyrrolidinone--, therefor.

Columns 19-20,
Line 45, Table 1, delete "Redisperible" and insert --Redispersible--, therefor.

In the Claims

Column 23,
Line 8, Claim 3, delete "thereof" and insert --thereof;--, therefor.